United States Patent [19]

Buckenham et al.

[11] Patent Number: 5,566,480
[45] Date of Patent: Oct. 22, 1996

[54] CREASE SETTING AND MEASURMENT

[75] Inventors: Peter Buckenham; Nhan G. Ly, both of New South Wales, Australia

[73] Assignee: Commonwealth Scientific and Industrial Research Organisation, Campbell, Australia

[21] Appl. No.: 244,600

[22] PCT Filed: Nov. 30, 1992

[86] PCT No.: PCT/AU92/00642

§ 371 Date: Jul. 5, 1994

§ 102(e) Date: Jul. 5, 1994

[87] PCT Pub. No.: WO93/11429

PCT Pub. Date: Jun. 10, 1993

[30] Foreign Application Priority Data

Dec. 3, 1991 [AU] Australia .................. PK9800

[51] Int. Cl.⁶ .................. D06F 71/36; B65H 45/12
[52] U.S. Cl. .................. 38/17; 73/159
[58] Field of Search .................. 38/1 B, 12, 15, 38/19, 28, 43, 64, 69, 70, 71; 73/159; 223/37, 38, 52.6, 57; 100/38, 40, 54, 92, 57, 935; 34/90, 143, 242, 414, 417, 419

[56] References Cited

U.S. PATENT DOCUMENTS

| | | | |
|---|---|---|---|
| 511,097 | 12/1893 | Shepard | 38/19 |
| 667,537 | 2/1901 | Lees | 220/358 |
| 2,309,617 | 1/1943 | Benson | 220/358 |
| 2,482,470 | 9/1949 | De Waard et al. | 73/159 X |
| 2,646,679 | 7/1953 | Buker | 73/159 X |
| 3,094,866 | 6/1963 | Sloan et al. | 73/159 |
| 3,095,737 | 7/1963 | Hollenbaugh et al. | 73/159 |
| 3,151,952 | 10/1964 | Turato | 34/143 X |
| 3,381,528 | 5/1968 | Adams et al. | 73/159 |
| 3,494,189 | 2/1970 | Copeland et al. | 73/159 |
| 3,507,149 | 4/1970 | Copeland et al. | 73/159 |
| 3,618,814 | 11/1971 | Nagroski | 220/358 |
| 4,017,980 | 4/1977 | Kleinguenther | 34/143 X |
| 4,674,650 | 6/1987 | Hamilton et al. | 220/358 X |

FOREIGN PATENT DOCUMENTS

| | | |
|---|---|---|
| 60021/90 | 1/1991 | Australia . |
| 46299/79 | 10/1991 | Australia . |
| 310165 | 10/1971 | U.S.S.R. ...... 73/159 |

OTHER PUBLICATIONS

Derwent Abstract Accession No. 26063 E/13, Class S03, SU, A 836591 (Cotton Ind Inst) 7 Jun. 1981.
Derwent Abstract Accession No. 88–219176/31, Class S03, SU, A 1366945 (MOSC, Light Ind. Tech.) 15 Jan. 1988.
Derwent Abstract Accession No. 83–843414/50, Class S03, SU, A, 996939 (Kaun Poly) 15 Feb. 1983.

Primary Examiner—Ismael Izaguirre
Attorney, Agent, or Firm—Heslin & Rothenberg, P.C.

[57] ABSTRACT

A method of setting a crease in a fabric for measurement of the fabric's crease setting performance whereby the fabric is conditioned to a predetermined water content level and then bent upon itself to form a crease therein, heated while maintaining the crease therein for a predetermined period under conditions which ensure that the water content of the fabric remains constant and, finally, rapidly cooled to set the crease. A fabric sample press cell includes a base which cooperates with a cap to enclose a chamber which is relatively narrow. The chamber receives a fabric sample folded back upon itself so that the fabric becomes creased. The base is sealingly connected to the cap by means of a resilient circular seal so that the sample is maintained sealingly enclosed within the chamber. Abutting the sample is a resilient disk which is backed by a resilient sheet. A clamp is provided to maintain the sample under pressure in the chamber to crease the sample.

9 Claims, 5 Drawing Sheets

CREASE SETTING AND MEASURMENT

FIELD OF THE INVENTION

This invention relates to the setting of creases in fabrics whereby the crease setting performance of a fabric may be reliably tested arc thereby standardised.

BACKGROUND OF THE INVENTION

Fabrics vary from each other in the sharpness of a crease which may be obtained in steam pressing operations performed on a garment made from the fabric. For example a high quality pure wool structured garment is pressed as one of the final processes in garment manufacturing. The aim of pressing is to give a smooth crisp appearance to the panels and seams of the garment. If during the pressing the seam can not be made flat and sharp, but tends to billow, then it is said to be "blown", seam blowing can make a high quality tool garment unacceptable for sale and is occurring with increasing frequency in light-weight fabrics.

The ability of a seam to press flat is not directly related to other fabric properties but can be modified during finishing. It is important therefore robe able to predict the performance in seam pressing of a fabric prior to cutting so that remedial measures can be taken where required.

If a sample of fabric is conditioned, folded and pressed, and allowed to recover, the angle of the crease can be measured and used to predict whether seam blowing will occur. When this value is related to other fabric properties such as weight and formability, it can be used to predict the overall appearance of the pressed seam.

In devising an appropriate test for predicting the crease setting performance of a fabric, it is necessary to bear in mind that fabric manufacturers will normally not have steam pressing apparatus available to them which is suitable as a test apparatus. Any apparatus that fabric manufacturers may have available, even if usable in a crease setting performance test, is liable to be subject to numerous unpredictable sources of error which would limit the value of the data obtained as a reliable predictor of a fabric's crease setting performance.

SUMMARY OF THE INVENTION

There is disclosed herein a method of forming a crease in a fabric for measurement of the fabric's crease setting performance comprising:
conditioning a sample of the fabric to a predetermined water content level;
bending the sample of fabric upon itself to form a crease therein;
heating the sample of fabric and maintaining the crease therein, for a predetermined period, under conditions which ensure that the water content of the fabric remains substantially constant; and
rapidly cooling the sample to set the crease.

There is further disclosed herein a fabric crease setting cell comprising:
a base having a press surface;
a cap having a press surface;
seal means joining the base and cap and cooperating therewith to provide a sealed chamber to receive a folded fabric sample, so that a sample located therein is sealingly enclosed within the chamber; and
clamp means maintaining said base and cap sealingly connected and placing said sample under pressure to crease the sample.

Preferably the crease in the fabric is maintained by an airtight enclosure which ensures maintenance of the predetermined water content. The temperature to which the fabric may be heated is preferably the temperature of boiling water under ambient conditions.

The sample of fabric may be conditioned by placing it in a room or enclosure under controlled conditions of humidity and/or temperature and/or pressure. Alternatively air of a predetermined humidity level may be blown or sucked through the fabric to achieve conditioning, Conditioning a sample of fabric can include providing a mesh upon which the fabric may be placed. Conditioned all passing through the mesh then conditions the sample.

The means for passing conditioned air through a fabric when it is positioned on the mesh may operate via a vacuum or a pressurised process.

The preferred form of the invention is particularly applicable to woven fabrics containing wool, but is not limited to such fabrics. By virtue of the preferred form of the invention, acceptably reproducible test results as to the "crease pressing performance" of fabrics are obtainable.

BRIEF DESCRIPTION OF THE DRAWINGS

The invention will now be described, by way of example only, with reference to the accompanying drawings in which.

DETAILED DESCRIPTION OF THE PREFERRED EMBODIMENTS

In conducting a creasing performance test, fabric samples 40 are conditioned in a room or enclosure maintained at 20° C. (±2° C.) and 65% relative humidity (±2% RH) for a predetermined period. For example they may be left in a conditioned room for 24 hours, or have conditioned air passed through them for about 1 hour.

Figure 1:
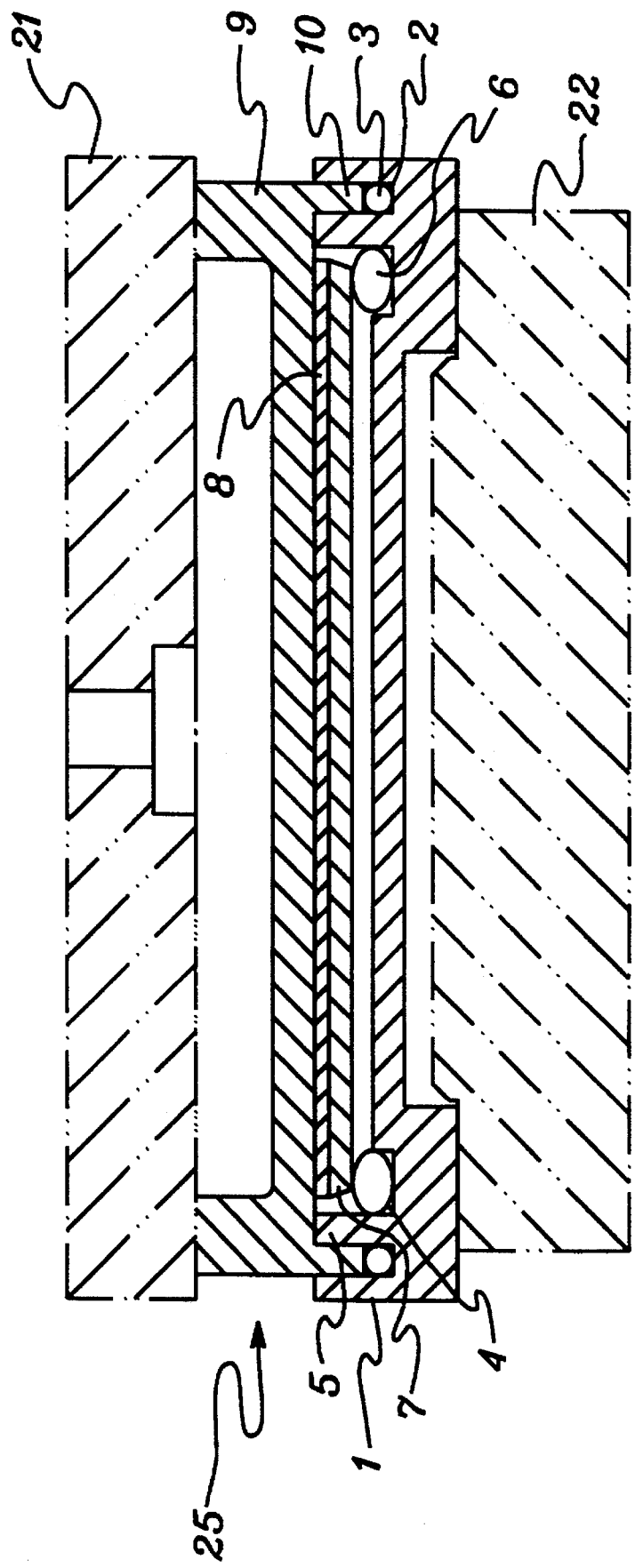
FIG. 1 is a cross-sectional view of a crease setting cell.

After conditioning in the standard atmosphere the fabric samples are folded and the fold in each sample is fixed, for example by stapling 41 (step I). The folded samples of fabric are then sealed in a cell of the second aspect of the invention, an example of which is illustrated in FIG. 1. The cell comprises a lower member or base plate 1 having an annular outer groove 2 within which an "0" ring 3 is seated. The base plate also includes an annular inner groove 4 and an upstanding annular flange 5 between the grooves 2 and 4. An annular silicone rubber t is seated in groove 4. A circular metal disc 7, the diameter of which is slightly less than the inner diameter of flange 5 and a silicone rubber sheet 8 (on top of disc 7) rest on the resilient tubing 6. The cell is completed by an upper member (cap) 9 which includes an annular depending flange 10 for seating onto the "0" ring 3 within groove 2. The "0" ring 3 provides a seal between the upper and lower members 1 and 9, between which a sealed narrow gap compartment (chamber) is thereby formed. The folded samples of the fabric are contained within this compartment between the lower face of upper member 9 and the facing surface of the rubber sheet 8, which rests on the disc 7, which in turn rests on the resilient tubing 6. The overall diameter of the cell may be in the order of 106 mm and its thickness, when assembled, about 25 mm.

Figure 2:
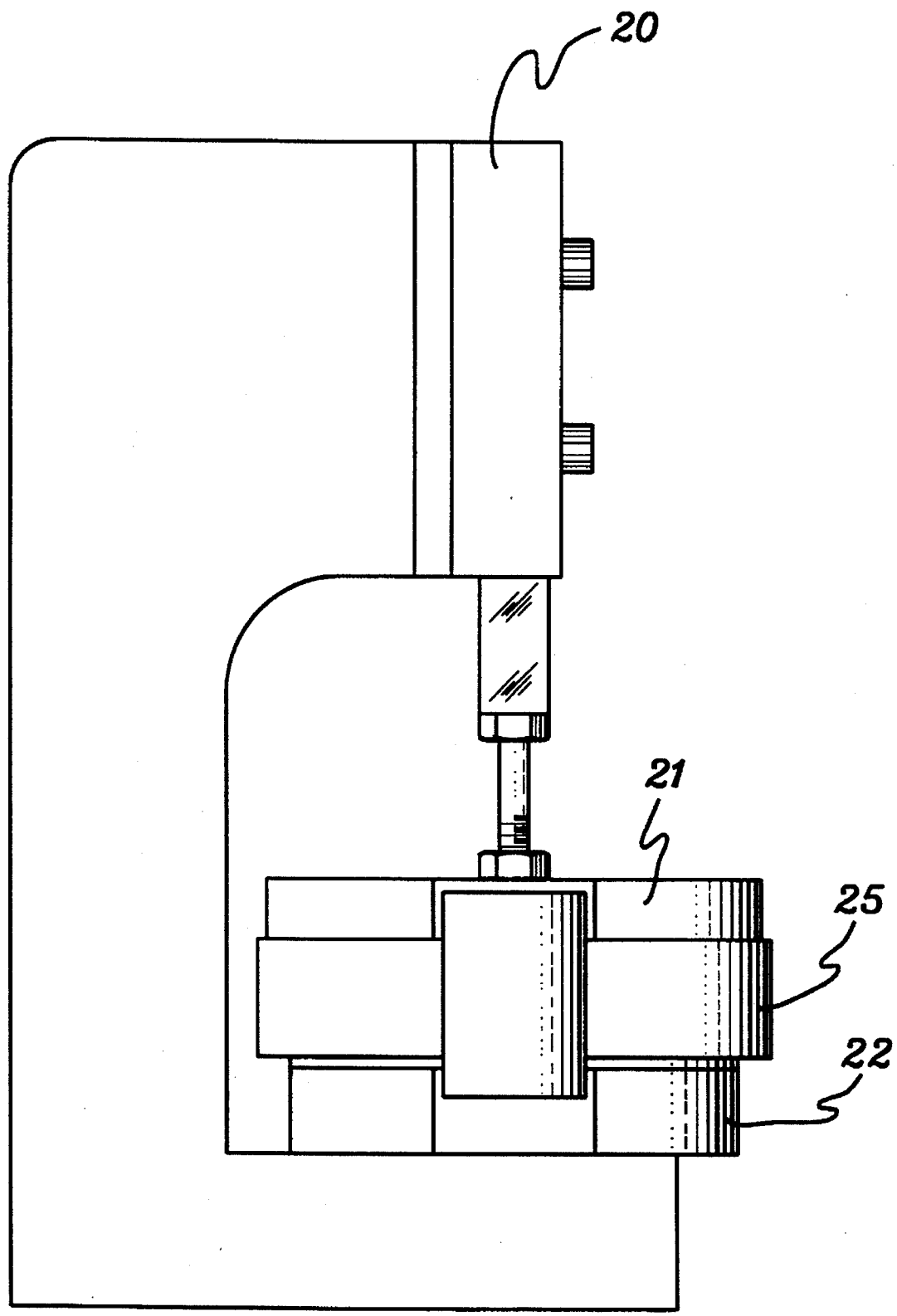
FIG. 2 shows a press for use with the cell of FIG. 1.
Figure 3A:
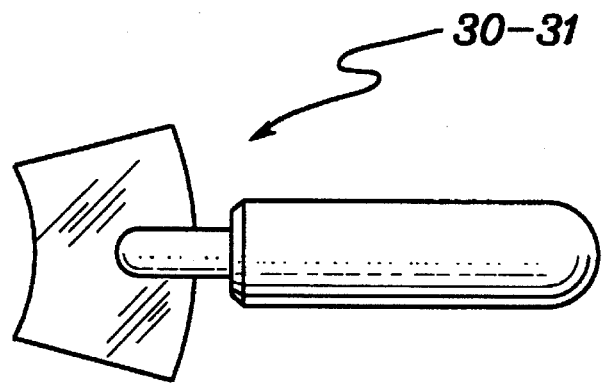
FIGS. 3a and 3b show a clamp for maintaining the cell of FIG. 1 sealed.
Figure 3B:
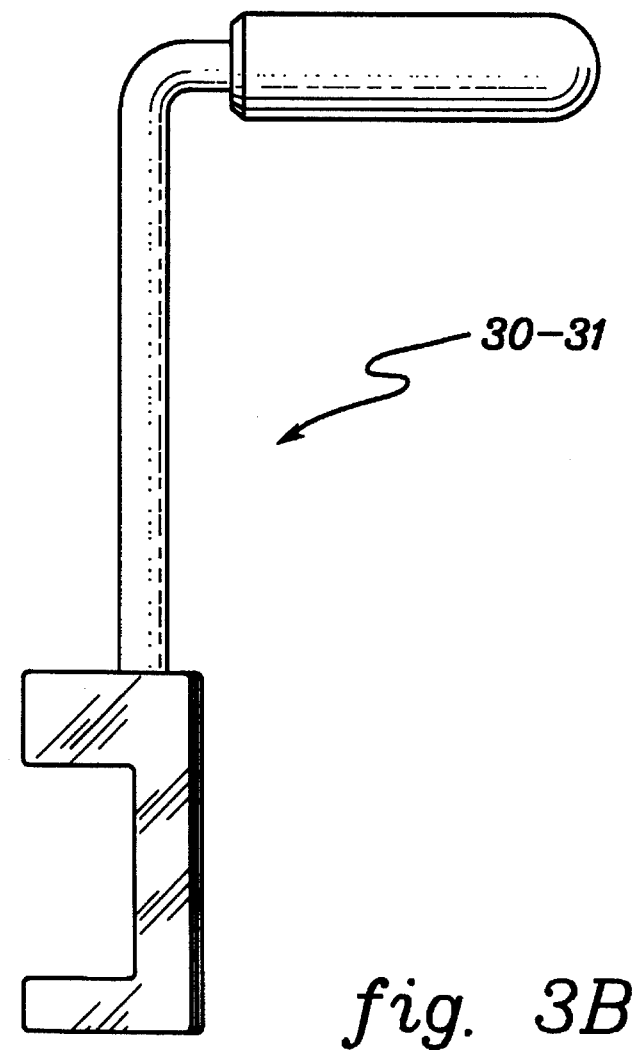
Figure 4:
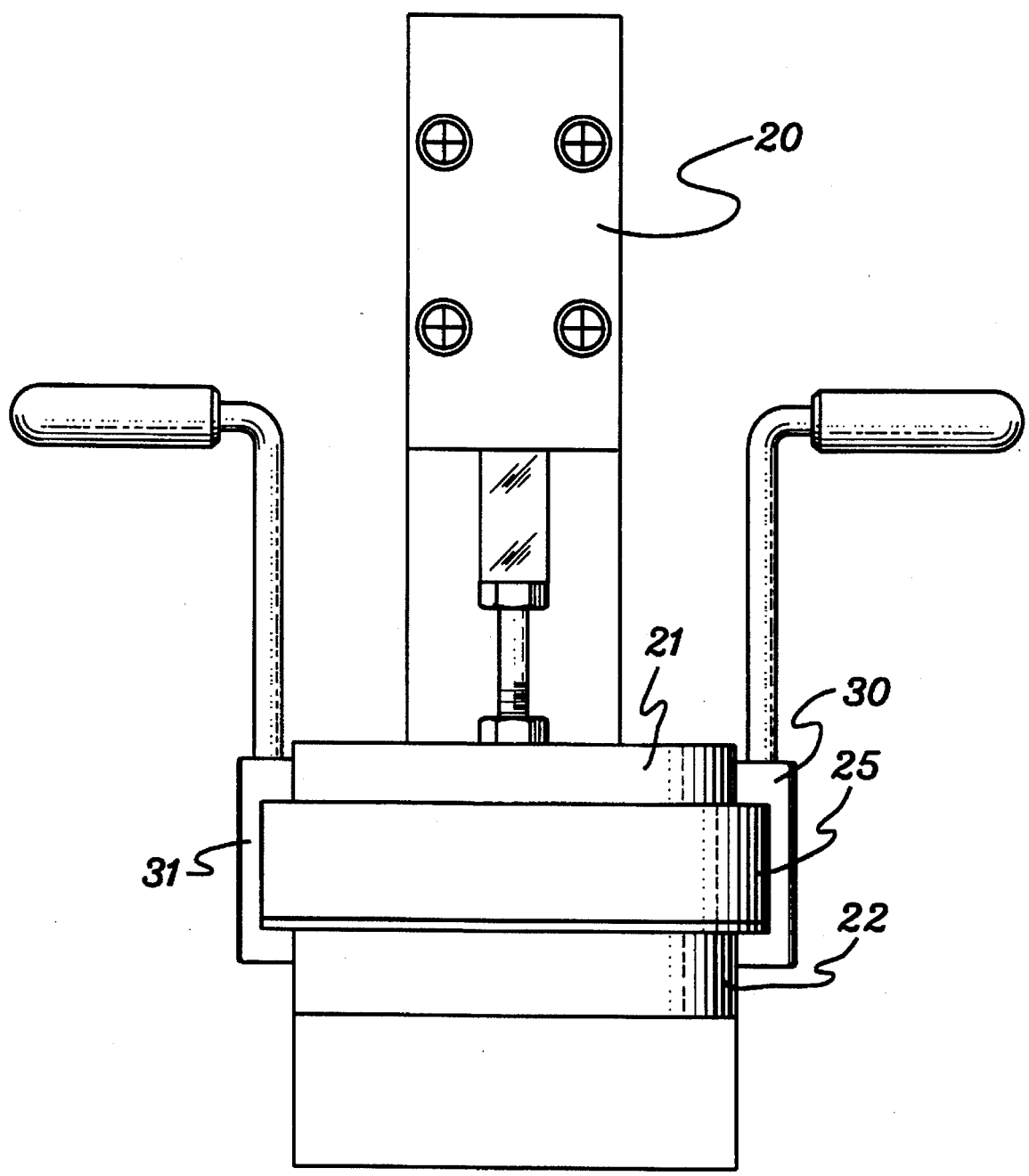
FIG. 4 shows a cell with clamps according to FIG. 3 attached thereto prior to removal of the cell-clamps assembly from a press.
Figure 5:
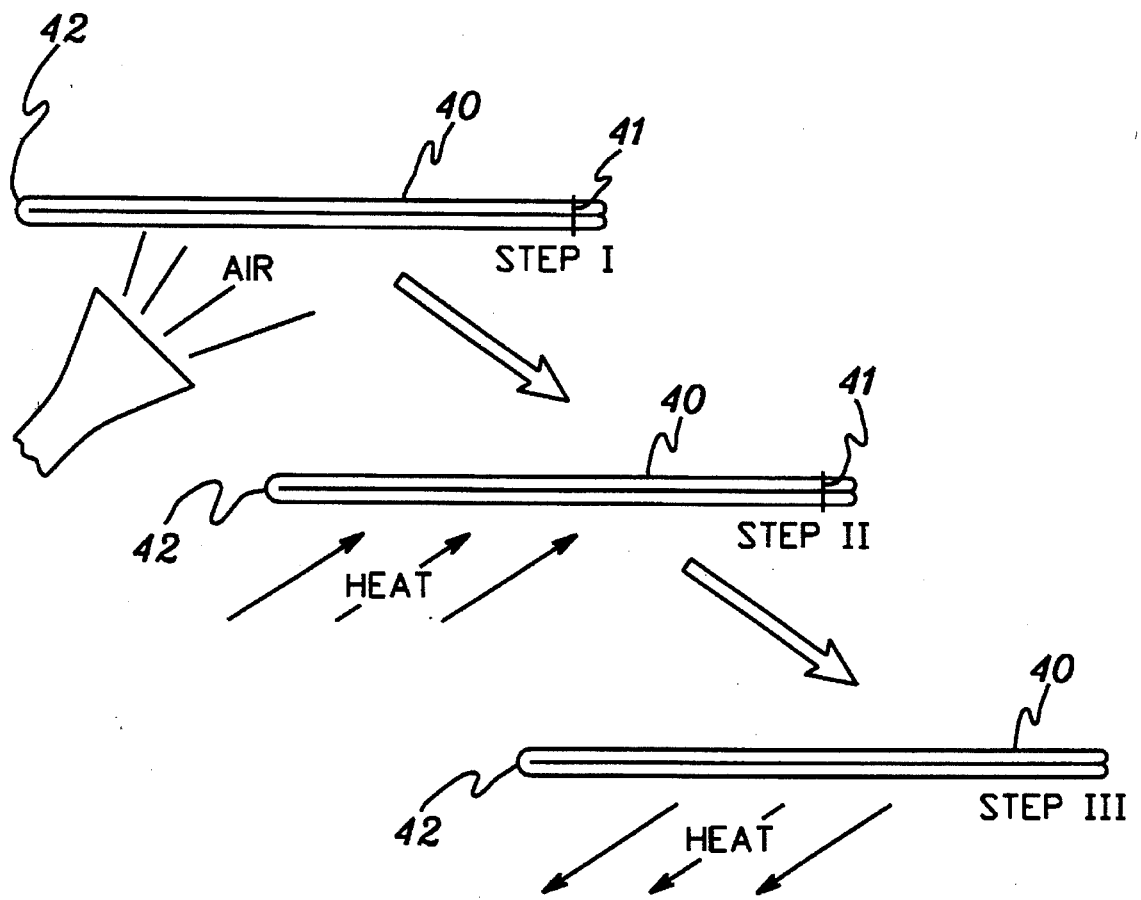
FIG. 5 is a Schematic flow diagram of a method of forming a crease in a fabric sample.

A press 20 (see FIG. 2) may be used to press the upper and lower members together. FIG. 2 illustrates an assembled cell 25 of FIG. 1 between plates 21 and 22 of press 20 (the press plates 21 and 22 ate also shown in outline in FIG. 1). A pair of clamps 30 and 31, an example of each being depicted in FIG. 3, are then placed over the assembled cell 25 while it is being pressed (see FIG. 4) such that when the press is released, the clamps maintain the cell in a sealed state, conveniently the clamps 30, 31 include handles (for example as illustrated) to facilitate handling of the cell while maintaining its seal. The sealed cell 25 is then immersed in boiling water for 3.5 minutes, which is maintained at the boil (step II), and then transferred to a water bath maintained at 20° C. for a further 3.5 minutes. The cell is then removed from the water and dried either with a towel or compressed air. It is then opened (by pressing to allow detachment of the clamps) and the samples removed. The sample is rapidly cooled to set the crease 42 (step III).

The samples are then cut with scissors to remove the staple and standardize the length of each arm of the fold, for example an arm length of 10 mm may be established. The samples are then left in the controlled atmosphere (20° C., 65% RH) for 24 hours. The staple should be removed soon after each sample is returned to the standard atmosphere, and the samples should be handled as little and as gently as possible. It is preferable to handle the samples with tweezers for example rather than fingers. Also, to ensure that there are no fibres tangled together which will hold the folds of the crease together, a piece of paper or thin card should be gently passed between the arms of each creased sample. The crease angles are measured 24 hours after pressing either directly with a suitable protractor, or by projecting the shadow of the crease onto a screen and measuring the projection. The angle should be measured from each side of each sample, giving two measurements for each sample.

The sealed cell enables the samples to be subjected to a temperature versus time regime with the regain of the fabric approximately constant, different thicknesses of fabric may be accommodated with approximately the same lateral pressure by means of the metal disc 7 supported by the annulus of silicon rubber tubing 6 which acts as a spring. Local compliancy to the shape of the crease is provided by the sheet 8 of silicon rubber. Also the upwardly facing surface of the disc 7 may be suitably marked (such markings being visible through rubber sheet 8) to provide a guide for the layout and alignment of samples within the cell.

Persons skilled in the art of metrology of fabrics will of course appreciate that various samples each of a standardised size from any given piece of fabric will be subjected to the test procedure. For example samples allowing measurement of the "warp crease angle" (the angle formed by the warp yarns at a pressed-in crease running parallel to the weft) and the "weft crease angle" (the angle formed by the weft yarns at a pressed-in crease running parallel to the warp) should be taken in sufficient number (for example 3 of each) to ensure a result of acceptable confidence.

Heat transfer between the cell and its surroundings takes place mainly through the upper metallic member 9. The method does not attempt to provide a temperature versus time regime as would be provided by a steam press as the rate of heat transfer provided by live steam and the applied vacuum is difficult to match, suitable times and lateral pressure for tests according to this invention are determinable by experiment to obtain the same crease angles for a range of fabrics, Those skilled in the art will appreciate that the invention described herein is susceptible to variations and modifications other than those specifically described and it is to be understood that the invention includes all such variations and modifications which fall within its spirit and scope.

We claim:

1. A method of forming a crease in a fabric for measurement of the fabric's crease setting performance comprising:

conditioning a sample of the fabric to a predetermined water content level;

bending the sample of fabric upon itself to form a crease therein;

heating the sample of fabric and maintaining the crease therein for a predetermined period, under conditions which ensure that said predetermined water content of the fabric remains substantially constant; and rapidly cooling the sample to set the crease.

2. The method of claim 1, further including providing press members and seals which co-operate to provide an airtight chamber, and wherein heating of the fabric takes place in said chamber.

3. The method of claim 2, wherein said chamber provides a narrow gap so that the sample located therein is placed under pressure.

4. The method of claim 3, wherein said members include a pair of cooperating plates between which said gap is defined, and said method further includes the steps of providing a first one of the first plates, mounting said sample on a press surface of said first plate, sealingly mounting the other plate on said first plate and pressing said plates together to apply pressure to said sample.

5. The method of claim 1 or 2, wherein said sample is heated to the temperature of boiling water.

6. The method of claim 1 or 2, wherein conditioning of said sample is achieved by moving air of a predetermined humidity through the fabric.

7. The method of claim 2 or 3, further including providing in and extending across said chamber to transmit pressure to said sample, a sheet of resilient material.

8. A fabric crease setting cell comprising:

a base having a press surface;

a cap having a press surface;

seal means joining the base and cap and cooperating therewith to provide a sealed chamber to receive a folded fabric sample, so that a sample located therein is sealingly enclosed with the chamber;

clamp means maintaining said base and cap sealingly connected and placing said sample under pressure to crease the sample;

a resilient sheet in said chamber; and a disc abutting said sheet, which disc engages said sample.

9. The press cell of claim 8, wherein said seal means includes a resilient ring encompassing said chamber and sandwiched between said cap and base.

* * * * *